US012642687B2

(12) United States Patent
Young et al.

(10) Patent No.: US 12,642,687 B2
(45) Date of Patent: Jun. 2, 2026

(54) COLOURED OSTOMY POUCH

(71) Applicant: ConvaTec Limited, Flintshire (GB)

(72) Inventors: Alice Young, Chester (GB); Sabrina Falloon, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 378 days.

(21) Appl. No.: 18/519,449

(22) Filed: Nov. 27, 2023

(65) Prior Publication Data

US 2024/0091049 A1 Mar. 21, 2024

Related U.S. Application Data

(63) Continuation of application No. PCT/GB2022/052026, filed on Aug. 2, 2022.

(30) Foreign Application Priority Data

Aug. 3, 2021 (GB) ...................................... 2111173

(51) Int. Cl.
| | |
|---|---|
| *A61F 5/445* | (2006.01) |
| *A61F 5/44* | (2006.01) |
| *A61F 5/443* | (2006.01) |
| *A61F 5/448* | (2006.01) |

(52) U.S. Cl.
CPC ............ *A61F 5/445* (2013.01); *A61F 5/4404* (2013.01); *A61F 5/443* (2013.01); *A61F 5/448* (2013.01)

(58) Field of Classification Search
CPC .......... A61F 5/445; A61F 5/443; A61F 5/448; A61F 5/4404
See application file for complete search history.

(56) References Cited

U.S. PATENT DOCUMENTS

| | | | | |
|---|---|---|---|---|
| 3,570,490 | A * | 3/1971 | Berger | .................... A61F 5/445 604/339 |
| 3,941,133 | A * | 3/1976 | Chen | ....................... A61F 5/443 604/336 |
| 10,076,438 | B2 * | 9/2018 | Bendix | .................... A61F 5/448 |
| 11,399,973 | B2 * | 8/2022 | Bendix | ................ A61F 5/4404 |
| 2002/0064614 | A1 * | 5/2002 | Turnbull | ................ B32B 5/022 428/35.4 |
| 2005/0261645 | A1 * | 11/2005 | Conrad | .................... A61F 5/445 604/332 |
| 2006/0228318 | A1 * | 10/2006 | Fabo | ................... A61F 13/0253 424/70.12 |
| 2008/0154220 | A1 * | 6/2008 | Gaffney | ................. A61F 5/445 604/339 |
| 2008/0269699 | A1 * | 10/2008 | O'Toole | ................. A61F 5/448 604/332 |
| 2008/0269700 | A1 * | 10/2008 | O'Toole | ............... A61F 5/4405 604/332 |
| 2009/0234312 | A1 * | 9/2009 | O'Toole | ................. A61F 5/448 604/332 |

(Continued)

*Primary Examiner* — Guy K Townsend
(74) *Attorney, Agent, or Firm* — TAFT STETTINIUS HOLLISTER LLP; Ryan O. White; Derek B. Lavender

(57) ABSTRACT

An ostomy pouch includes a front wall, a rear wall and an inlet for receiving human waste. The pouch has a comfort layer provided at least on the front wall. The comfort layer on the front wall has a colour with a value in the range L*=50.0 to 70.0, a*=+1.8 to +10.0 and b*=−0.9 to −9.0 or +0.9 to +12.0 measured in the CIE L*a*b* colour code system.

20 Claims, 2 Drawing Sheets

(56)  References Cited

U.S. PATENT DOCUMENTS

| 2012/0179124 | A1* | 7/2012 | Nguyen-Demary | .... A61F 5/448 |
| | | | | 604/335 |
| 2013/0035653 | A1* | 2/2013 | Kannankeril | .......... A61F 5/445 |
| | | | | 493/267 |
| 2013/0116636 | A1* | 5/2013 | Carrubba | ................ A61F 5/448 |
| | | | | 604/318 |
| 2013/0156983 | A1* | 6/2013 | Pham | ...................... B32B 27/08 |
| | | | | 428/36.7 |
| 2014/0296807 | A1* | 10/2014 | Bendix | .................. A61F 5/445 |
| | | | | 604/332 |
| 2018/0333290 | A1* | 11/2018 | Jones | ...................... A61F 5/443 |
| 2018/0353317 | A1* | 12/2018 | Bendix | .................. A61F 5/443 |
| 2021/0100678 | A1* | 4/2021 | Hoggarth | ............. A61F 5/4404 |
| 2024/0091049 | A1* | 3/2024 | Young | ................... A61F 5/445 |
| 2024/0252344 | A1* | 8/2024 | Hill | ...................... A61F 5/4404 |

* cited by examiner

COLOURED OSTOMY POUCH

TECHNICAL FIELD OF THE INVENTION

The present invention relates to an ostomy pouch for managing effluent from a stoma. In particular it relates to an ostomy pouch having a particular colour.

BACKGROUND TO THE INVENTION

There are many forms of ostomy pouch, for example, open and closed, one-piece or two-piece. Pouches may have various shapes and various components. Typically they comprise a cavity formed of a (normally plastic) film, frequently formed by two layers, front and rear, welded together at their periphery, with the rear layer of film (closest to the ostomate's body in use) including an aperture through which effluent can enter the pouch.

For use in hospital environments, it is not uncommon to omit the comfort layer and have an outermost film layer which is transparent, to allow easy inspection by health care professional. However, for personal use, foremost layer will typically be an opaque.

The opaque foremost layer can be a film layer. However, for the comfort of the ostomate, a "comfort layer" is often provided, overlying the rear film layer, and normally the front film layer too. The comfort layer is made of a material that is more comfortable against the skin than the film, and which may interact better with clothing e.g. a woven or non-woven fabric. Where a comfort layer is provided, in order that an ostomate can inspect to contents of the pouch, the front layer of the film is often transparent, whilst the foremost comfort layer is opaque, but includes an opening, that is normally closed, but can be opened by the ostomate to view the contents.

Historically, as outlined in EP2755613 ostomy pouches were typically all provided in a pink colour to simulate Caucasian flesh tone. This approach to hiding the pouch by seeking to blend in with the flesh was flawed. In addition to a racial insensitivity in failing to even seek to match non-Caucasian flesh tones, there are many different Caucasian flesh tones and an individual's flesh tone may change seasonally, or even from day to day (e.g. tanning, or burning in the sun), so the pink frequently fails to match. It also suffers from looking "clinical" if it is noticed.

EP2755613 therefore proposes collection pouches having a particular greyish colour, which it explains is less visible under a thin piece of garment than bags of traditional colour, and if noticed, might appear to be a fashion accessory, or other common object, not a medical appliance. Specifically, EP2755613 proposes a collection bag wherein at least the front wall has a colour with a value in the range of L*=60.0 to 80.0, a*=−1.5 to +2.0 and b*=+1.5 to +9.0 measured in the well known CIE L*a*b* colour code system described therein Unfortunately, these greyish collection pouches suffer another more esoteric problem; surprisingly, the inventors have identified that if the greyish colour is applied to a comfort layer rather than a film layer, when a pouch so-formed gets wet, for example in the shower or when bathing or swimming, the comfort layer becomes somewhat see-through. This would be an issue especially for pouches with a transparent front film layer and a greyish comfort layer, because the contents of the pouch (e.g. stomal liquid/solids) would become visible, potentially causing embarrassment.

WO2005109983A2 proposes an ostomy pouch primarily aimed at children which also addresses the "clinical" appearance of standard pink-skin coloured pouches. Instead of hiding the pouch, its approach is make it appear like a fashion accessory or other common object. To achieve this, it is proposed to make the pouch in the shape of a recognisable iconic shape, for example a teddy bear and to construct it from a coloured plastic, preferably black, brown, red, orange, yellow, green, blue, violet, grey and/or white. Fibres may be applied to the surface of the pouch by electrostatic flocking, which are said to "form an appearance similar to cloth or other textiles", but there is no suggestion of a comfort layer and as such these pouches would not suffer the problem identified in respect of transparency when wet.

It is an object of embodiments of the present invention to at least partially overcome or alleviate the above problems.

SUMMARY OF THE INVENTION

In this specification, the term "stomal output" primarily refers to fluids or solids produced by an ostomate that may be secreted from the stoma or that exit the stoma. The stomal output may comprise stomal gas, stomal liquid and stomal solids, but as the invention concerns visible output, stomal gas is less relevant.

In this specification, the term "stoma" refers to an opening in the body. Generally the stoma is a surgical opening in the torso of the body. In some instances, the term "stoma" also refers to internal tissue, organs or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy pouch disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy pouches disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, a urostomy, a nephrostomy, an ureterostomy, or a vesicostomy. The ostomy pouches disclosed herein may be used with additional devices including, but not limited to, a shunt, a catheter, a plug or a fecal management system.

In this specification locations and orientations of features may be described with reference to the ostomy pouch being "in use", "orientated as it would be in use" or similar. Such terms refer to the intended orientation of the ostomy pouch when it is adhered to a body of an ostomate with the ostomate in a standing position, irrespective of whether the ostomy pouch is currently performing such a use or the actual position of the ostomate. The terms "upper" and "lower" and related terms refer to the relative position of a part or portion of the ostomy pouch when orientated as it would be in use. For example, a section of the ostomy pouch may be referred to as an "upper" section of the ostomy pouch. In such an example, said section will be intended to be the uppermost section (in the vertical direction) of the ostomy pouch when attached to the body of a standing ostomate. However the reader skilled in the art will appreciate that before attachment to the ostomate said section may not always be the uppermost section and in addition when attached the section may not always be the uppermost section if the ostomate adopts a non-standing position, for example lying down.

The terms "left" and "right" and related terms refer to the ostomy pouch when viewed from the rear. Thus, as an illustrative example, a "left" edge of the ostomy pouch will be towards a left-hand side of the ostomate in the situation where the ostomy pouch is attached to the front torso of the ostomate.

In this specification the terms "front" and "rear" refer to the relative position of a part or portion of the ostomy pouch with reference to the body of an ostomate when the ostomy pouch is attached to the body. "Rear" refers to a position relatively closer to the body of the ostomate than a comparative position that is "front". "Front" refers to a position relatively further away from the body of the ostomate than a comparative position that is "rear".

In this specification the term "peripheral" refers to a portion situated on or towards an edge of the item being referred to.

Ostomy pouches are commonly attached to the body by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." In this specification, the term "ostomy wafer" includes ostomy wafers for a "two-piece pouch" and for a "one-piece pouch".

In this specification a "two-piece pouch" refers to a pouch where the ostomy wafer forms part of a separate body fitment component that is attached by a releasable coupling to the remainder of a pouch. A two-piece pouch permits the body fitment component to be separated from the pouch without damage, so that at least one of the parts continues to be functionally usable. For example, the body fitment component may remain in place on the body of the ostomate.

In this specification a "one-piece pouch" refers to a pouch where the ostomy wafer is permanently attached to the pouch, to the extent that the ostomy wafer cannot easily be separated without risk of damaging the pouch. A one-piece pouch is intended to be used as an integral unit.

Ostomy pouches are commonly configured as closed pouches or open pouches. In this specification a "closed pouch" refers to an pouch where it is not intended that stomal output is drained from the cavity. Thus, a closed pouch may typically be configured as a one-use, disposable and non-reusable pouch. In this specification an "open pouch" refers to an pouch where it is intended that stomal output is drained from the cavity. Thus, an open pouch may be configured as a reusable pouch, such that it can be reused and emptied multiple times whilst attached to the body, although this is not essential. In an open pouch the stomal output may be drained intermittently as instigated by an action of the ostomate or may be drained intermittently or continuously due to the cavity being fluidly connected to a drain, for example a night drain line.

According to a first aspect of the present invention, there is provided an ostomy pouch comprising a front wall, a rear wall and an inlet for receiving human waste; the pouch having a comfort layer provided at least on the front wall; wherein at least the comfort layer on the front wall has a colour with a value in the range of $L^*$=50.0 to 70.0, $a^*$=+1.8 to +10.0 and $b^*$=−0.9 to −9.0 or +0.9 to +12.0 measured in the CIE $L^*a^*b^*$ colour code system (described herein). More preferably the colour has a value in the range of $L^*$=50.0 to 70.0, $a^*$=+1.8 to +10.0 and $b^*$=−0.9 to −9.0 or +1.0 to +12.0

Notably, this "goldilocks" region, with a positive $a^*$ value indicating colours that are redder than they are green, encompasses embodiments which exhibit low transparency when wet, along with acceptable levels of visibility under clothing and good racial sensitivity (not approximating Caucasian skin tones).

In the CIE $L^*a^*b^*$ system, the value of $L^*$ relates to the darkness of the colour (white is 100, black is 0). This $L^*$ value is considered to be important to discretion.

The $a^*$ value is the red/green co-ordinate, where a positive value is red and a negative value is green. The magnitude of the minimum boundary of this value is considered relevant to maintaining opacity whilst wet, whilst it is considered that the minimum boundary ensures that the colour is not too saturated, because a brilliant, intense, vivid colour would lack discretion.

The $b^*$ value is the yellow/blue co-ordinate, where a positive value is yellow and a negative value is blue. It will be noted that colours in both the positive and negative are acceptable, but there should be at least some blue/yellow. Thus, the minimum boundary of blueness/yellowness (i.e. −0.9 or +0.9, preferably +1.0) provides a colour that is not too pink (and racially insensitive), whilst the maximum boundary (i.e. −9.0 or +12.0) ensures that the colour is not too saturated and is therefore sufficiently discreet.

In one preferred range $L^*$=50.0-59.9. As compared to the prior art, this is a fairly dark colour, with $L^*$ lower than even the bottom of the range claimed in EP' 613 and substantially lower than the actual embodiments disclosed therein. Comfort layers with such values are especially effective in avoiding transparency when wet.

In another preferred range $L^*$=60.0-70.0. As compared to the prior art, this is relatively low; embodiments having such a level of $L^*$ (in combination with the $a^*$ and $b^*$ values of the invention offer good opacity when wet, whilst performing well in terms of visibility under clothing too.

In another preferred range, $b^*$ is +0.9 to +12.0, more preferably +1.0 to +12.0. In particular within the range, but also more generally, sub-ranges in which $a^*$ is +1.8 to +3.0, +2.1 to +10.0 or +9.0 to +10.0 are preferred and sub-sub ranges where $a^*$ is +1.8 to +2.0, +2.4 to +2.6, or +9.3 to +9.5 are especially preferred. In particular in combination with the sub-range and sub-sub ranges discussed, but also more generally, it is preferred that $b^*$ is +2.0 to +12 and more preferably either +2.0 to +2.2 or +8.5 to +12, more particularly, +8.5 to +8.9 or +11.3 to +11.7. In one preferred embodiment $a^*$ is +1.8 to 2.0 and $b^*$ is +8.5 to +8.9; in another preferred embodiment $a^*$ is +2.4 to +2.6 and $b^*$ is +2.0 to +2.2; and in another preferred embodiment $a^*$ is +9.3 to +9.5 and $b^*$ is +11.3 to +11.7.

Another preferred range has $b^*$ of −0.9 to −9.0. within this range, but also more generally it is preferred that $a^*$ is +2.1 to +10.0. In particular within this range, but also more generally a sub-range in which $b^*$ is −4.0 to −6.0 is preferred, and a sub-sub-range in which $b^*$ is −4.5 to −5.5 is more preferred. In particular within this range, but also more generally, one sub-range in which $a^*$ is +1.8 to +7.0 is preferred and another where $a^*$ is 2.1 to 7.0 and sub-sub ranges in which $a^*$ is +1.8 to +2.0 or +6.5 to +7.0. Of course it is most preferred if the sub-ranges and/or sub-sub ranges are combined; in one preferred embodiment, b* is −4.0 to −6.0 and a* is +1.8 to +7.0; in a more preferred embodiment b* is −4.5 to −5.5 and a* is +1.8 to +7.0; in one preferred embodiment b* is −4.0 to −6.0 and a* is +1.8 to +2.0 or +6.5 to +7.0; in a most preferred embodiment b* is −4.5 to −5.5 and a* is +1.8 to +2.0 or +6.5 to +7.0.

Of course, it is even more preferred for these preferred ranges of a* and b* to be combined with the preferred ranges of L* set out above, or even with sub-ranges of L* such as 50.0 to 55.0 or 65.0 to 70.0 so the invention provides preferred embodiments as follows:

L* is 50.0-59.9 and b* is +0.9 to +12.0, or more preferably +1.0 to +12.0. In particular within the range sub-ranges in which a* is +1.8 to +3.0, +2.1 to +10.0 or +9.0 to +10.0 are preferred and sub-sub ranges where a* is 1.8 to 2.0, +2.4 to +2.6, or +9.3 to +9.5 are especially preferred. In particular in combination with the sub-range and sub-sub ranges discussed, but also more generally, it is preferred that b*is +2.0 to +12 and more preferably either +2.0 to +2.2 or +8.5 to +12, more particularly, +8.5 to +8.9 or +11.3 to +11.7. In one preferred embodiment L* is 50.0-59.9 a* is +1.8 to 2.0 and b* is +8.5 to +8.9; in another preferred embodiment L* is 50.0-59.9 a* is +2.4 to +2.6 and b* is +2.0 to +2.2; and in another preferred embodiment L* is 50.0-59.9 a* is +9.3 to +9.5 and b* is +11.3 to +11.7.

L* is 50.0-59.9 and b* is −0.9 to −9.0. within this range, it is preferred that a* is +2.1 to +10.0. In particular within this range, a sub-range in which b* is −4.0 to −6.0 is preferred, and a sub-sub-range in which b* is −4.5 to −5.5 is more preferred. In particular within this range, one sub-range in which a* is +1.8 to +7.0 is preferred and another where a* is 2.1 to 7.0 and sub-sub ranges in which a* is +1.8 to +2.0 or +6.5 to +7.0. Of course it is most preferred if the sub-ranges and/or sub-sub ranges are combined; in one preferred embodiment, L* is 50.0-59.9 b* is −4.0 to −6.0 and a* is +1.8 to +7.0; in a more preferred embodiment L* is 50.0-59.9 b* is −4.5 to −5.5 and a* is +1.8 to +7.0; in one preferred embodiment L* is 50.0-59.9 b* is −4.0 to −6.0 and a* is +1.8 to +2.0 or +6.5 to +7.0; in a most preferred embodiment L* is 50.0-59.9 b* is −4.5 to −5.5 and a* is +1.8 to +2.0 or +6.5 to +7.0.

L* is 60.0-70.0 and b* is +1.0 to +12.0. In particular within the range sub-ranges in which a* is +1.8 to +3.0, +2.1 to +10.0 or +9.0 to +10.0 are preferred and sub-sub ranges where a* is 1.8 to 2.0, +2.4 to +2.6, or +9.3 to +9.5 are especially preferred. In particular in combination with the sub-range and sub-sub ranges discussed, but also more generally, it is preferred that b*is +2.0 to +12 and more preferably either +2.0 to +2.2 or +8.5 to +12, more particularly, +8.5 to +8.9 or +11.3 to +11.7. In one preferred embodiment L* is 60.0-70.0 a* is +1.8 to 2.0 and b* is +8.5 to +8.9; in another preferred embodiment L* is 60.0-70.0 a* is +2.4 to +2.6 and b* is +2.0 to +2.2; and in another preferred embodiment L* is 60.0-70.0 a* is +9.3 to +9.5 and b* is +11.3 to +11.7.

L* is 60.0-70.0 and b* is −0.9 to −9.0. within this range, it is preferred that a* is +2.1 to +10.0. In particular within this range, a sub-range in which b* is −4.0 to −6.0 is preferred, and a sub-sub-range in which b* is −4.5 to −5.5 is more preferred. In particular within this range, one sub-range in which a* is +1.8 to +7.0 is preferred and another where a* is 2.1 to 7.0 and sub-sub ranges in which a* is +1.8 to +2.0 or +6.5 to +7.0. Of course it is most preferred if the sub-ranges and/or sub-sub ranges are combined; in one preferred embodiment, L* is 60.0-70.0 b* is −4.0 to −6.0 and a* is +1.8 to +7.0; in a more preferred embodiment L* is 60.0-70.0 b* is −4.5 to −5.5 and a* is +1.8 to +7.0; in one preferred embodiment L* is 60.0-70.0 b* is −4.0 to −6.0 and a* is +1.8 to +2.0 or +6.5 to +7.0; in a most preferred embodiment L* is 60.0-70.0 b* is −4.5 to −5.5 and a* is +1.8 to +2.0 or +6.5 to +7.0.

L* is 65.0-70.0 and b* is +1.0 to +12.0. In particular within the range sub-ranges in which a* is +1.8 to +3.0, or +2.1 to +10.0 are preferred and a sub-sub ranges where a* is +2.4 to +2.6 is especially preferred. In particular in combination with the sub-range and sub-sub ranges discussed, but also more generally, it is preferred that b*is +2.0 to +12 and more preferably +2.0 to +2.2. In one preferred embodiment L* is 65.0-70.0 a* is +2.4 to +2.6 and b* is +2.0 to +2.2.

L* is 50.0-55.0 and b* is +1.0 to +12.0. In particular within the range sub-ranges in which a* is +1.8 to +3.0, +2.1 to +10.0 or +9.0 to +10.0 are preferred and sub-sub ranges where a* is 1.8 to 2.0, or +9.3 to +9.5 are especially preferred. In particular in combination with the sub-range and sub-sub ranges discussed, but also more generally, it is preferred that b*is +2.0 to +12 and more preferably +8.5 to +12, more particularly, +8.5 to +8.9 or +11.3 to +11.7. In one preferred embodiment L* is 50.0-55.0 a* is +1.8 to 2.0 and b* is +8.5 to +8.9; in another preferred embodiment L* is 50.0-55.0 a* is +9.3 to +9.5 and b* is +11.3 to +11.7.

L* is 50.0-55.0 and b* is −0.9 to −9.0. within this range, it is preferred that a* is +2.1 to +10.0. In particular within this range, a sub-range in which b* is −4.0 to −6.0 is preferred, and a sub-sub-range in which b* is −4.5 to −5.5 is more preferred. In particular within this range, one sub-range in which a* is +1.8 to +7.0 is preferred and another where a* is 2.1 to 7.0 and sub-sub ranges in which a* is +1.8 to +2.0 or +6.5 to +7.0. Of course it is most preferred if the sub-ranges and/or sub-sub ranges are combined; in one preferred embodiment, L* is 50.0-55.0 b* is −4.0 to −6.0 and a* is +1.8 to +7.0; in a more preferred embodiment L* is 50.0-55.0 b* is −4.5 to −5.5 and a* is +1.8 to +7.0; in one preferred embodiment L* is 50.0-55.0 b* is −4.0 to −6.0 and a* is +1.8 to +2.0 or +6.5 to +7.0; in a most preferred embodiment L* is 50.0-55.0 b* is −4.5 to −5.5 and a* is +1.8 to +2.0 or +6.5 to +7.0.

Effectively, the goldilocks range encompasses a warm colour, reddish, but by no means a colour that would strike the average consumer as red or pink, indeed a colour so muted and low in saturation that its colour may be difficult for the average consumer to identify, yet at the same time not simply grey. A colour exemplified for example by PANTONE 15-3800 TPX "Porpoise"; Pantone 18-3710 TCX "grey ridge"; Pantone 18-4017 "Night Owl"; Pantone 18-1321 TCX "Brownie"; and Pantone 18-1108 TCX "Fallen Rock".

An environmental benefit stems from the provision of a comfort layer on the front wall in to goldilocks range: because of the excellent opacity whilst wet, it is postulated that an ostomate can go swimming, or undertake similar activities, with a partially full ostomy pouch, confident that the unsightly contents will not be seen. This means that a fresh pouch need not be put on before undertaking that activity, avoiding the unnecessary disposal of only partially used pouches.

The comfort layer may be a single colour having the same value in the CIE L*a*b* colour code system (described herein) across its entire surface.

Alternatively, the colour of the comfort layer may vary across the surface. Thus, the comfort layer may have different colours having differing values in the CIE L*a*b* colour code system (described herein) across its surface. The different colours across the surface may include colour values within and outside the range defined in the CIE L*a*b* colour code system (described herein). The values of the different colours across the surface may be entirely within the range defined in the CIE L*a*b* colour code system (described herein). The different colours across the surface may blend into each other. The different colours across the surface may be distinct, e.g. provided in distinct patches of different colours. Distinct patches of variable colours may make up a pattern. The pattern of patches of variable colour may be random.

The comfort layer may have a single colour intensity (chroma, C* in the CIE L*a*b* colour code system described herein). Alternatively, the intensity (chroma, C*) may vary across the comfort layer.

Where colour varies across the surface, the L* value may vary by no more than 30 between its highest value and its lowest value.

The ostomy pouch may further comprise a comfort layer on the rear wall. The comfort layer on the rear wall may have the same colour as the comfort layer on the front wall. This can be beneficial for example in making it easy to quickly identify the front and rear of the pouch.

The front wall on which at least one comfort layer is formed may be transparent. The front wall on which at least one comfort layer is formed may be translucent. There may be no intervening walls, in particular no opaque intervening walls between the front wall and the comfort layer provided thereon. The at least one comfort layer formed on the front wall may be spaced from the front wall. An opening may be provided in the comfort layer provided in the front wall, through which an ostomate may inspect stomal output.

The comfort layer may comprise a sheet of comfort material. The comfort material may be a woven material. Alternatively it may be a non-woven material. The comfort material may be absorbent.

The comfort material may comprise a natural material, for example cotton or wool and/or a synthetic material, for example any one or more of polyester, nylon, viscose, polyethylene, polypropylene, or the like. The comfort material may have an area density of 20 to 200 g/m², preferably 40-80 g/m², for example 58 g/m². The comfort material may have a tensile strength of 200 to 800 N, preferably 250 to 750 N, for example 620N in the warp and 620N in the weft. The comfort material may have a tear strength of 5 to 50 N, preferably 10-30N, for example 16 N. The comfort material may have a colour fastness to any one or more of rubbing, perspiration or washing (40°) of 4 to 5. The comfort material may have an abrasion of >50,000 rub cycles.

The comfort layer may have a thickness of 50 to 1000 micrometres, preferably 60 to 500 micrometres, more preferably 75 to 300 micrometres.

The comfort material may be a sheet having an outside surface and an opposite inside surface. The outside surface of the sheet of comfort material may form at least part of the outside surface of the pouch. At least part of the sheet of comfort material may have a hot-melt adhesive applied thereto.

The hot melt adhesive may be applied to the inside surface of the sheet of comfort material. The hot-melt adhesive may be applied as a web. The hot melt adhesive may be coated on the inner surface of the sheet of comfort material.

Where the pouch comprises two or more sheets of comfort material, any one of more of these sheets (and preferably both) may have an outside surface which forms at least part of the outside surface of the pouch and an opposite inside surface; wherein at least part of the inside surface of the sheet of comfort material is coated with a web of hot-melt adhesive.

The hot-melt adhesive may comprise any suitable type of hot-melt adhesive.

The web of hot melt adhesive may comprise a mass and a plurality of voids in the mass. The web may be a lattice, mesh or grid. The web may be a net or dots. The voids may be regularly spaced. The voids may be irregularly spaced. The voids may be regularly shaped. The web may have a regular and consistent distribution of adhesive. The voids may be irregularly shaped. The web may have an irregular and inconsistent distribution of adhesive. Each void may contain an absence (i.e. a substantial absence) of hot-melt adhesive applied to the woven fabric layer compared to the mass.

The voids may make up at least 20%, at least 30%, at least 40%, at least 50%, at least 60%, or at least 70% of the web.

The ostomy pouch may comprise a cavity for storing stomal output. The cavity may be defined by the rear wall and the front wall. The rear wall and front wall may be substantially the same shape. The rear wall and front wall may be joined at their peripheries. The rear wall and front wall may be formed of flexible sheet material, for example plastics film. The rear wall may be opaque. The rear wall and front wall may have corresponding inside and outside surfaces. The inside surfaces of the rear and front walls may form the interior of the cavity. The outside surfaces of the rear and front walls may form the exterior of the cavity. The comfort layer may cover the outside surface of the front wall, but may be spaced from and separable from the front wall. The comfort layer may be substantially the same shape as the front wall.

The comfort material covering the front of the pouch may comprise one or more parts; for example it may comprise two or more parts, such as an upper part and a lower part. The upper part and lower part when taken together may be the same shape as the front wall. The upper part may extend from a top edge of the pouch to a point 20-50% down its length from the top. The lower part may extend from a bottom edge of the pouch to a point 15-50% down its length from the top. An overlap region may be provided where the upper part and lower part overlap. The opening may be provided in the overlap region. The upper part may extend over the lower part (or vice versa) to form the overlap in the overlap region. The hot melt adhesive may be provided on one or both parts in the overlap region. In particular, the hot-melt adhesive may be provided on one or both parts at a periphery of the pouch, so as to ensure that these edges of the overlap region are bonded and the overlying part does not flap around. The upper part and the lower part may be separable from each other in the overlap region. The overlap region may extend horizontally when the ostomy pouch is in use. Thus, especially when the front wall is formed of a transparent/translucent film, the present invention provides a device that can permit convenient viewing of the stoma and/or the contents of the pouch if required.

Where the comfort material covering the front of the pouch comprises more than one part, at least one part, but more preferably each part least of the comfort layer on the front wall has a colour with a value in the range of L*=50.0 to 70.0, a*=+1.8 to +10.0 and b*=−0.9 to −9.0 or +0.9 to
+12.0 (or more preferably +1.0 to +12.0) measured in the
CIE L*a*b* colour code system (described herein). Each
part may have a colour with a value within any one of the
narrower ranges identified above. Moreover, each part of the
comfort material covering the front of the pouch may have
the same colour.

The pouch may comprise a drain. The drain may be
disposed at the bottom of the pouch in use. The drain may
have a front wall and a rear wall. The front wall and the rear
walls of the drain may be formed from the front and rear
walls of the pouch. The drain may be rectangular. The drain
may be foldable. The drain may be foldable along its length.
The drain may be movable between a folded and unfolded
configuration. The drain may be in a closed state in its folded
configuration. The drain may be in an open state in its
unfolded configuration. When open, the drain may permit
stomal output to leave the cavity of the pouch. When closed,
the drain may prevent stomal output leaving the cavity of the
pouch.

The rear wall of the drain may have a colour with a value
in the range L*=50.0 to 70.0, a*=+1.8 to +10.0 and b*=−0.9
to −9.0 or +0.9 to +12.0 (or more preferably +1.0 to +12.0)
measured in the CIE L*a*b* colour code system (described
herein). The rear wall of the drain may have a colour with
a value in any one of the narrower ranges identified above
in respect of the comfort layer on the front wall. Moreover,
the colour of the rear wall may be in the same narrower
range as the comfort layer on the front wall. The front wall
of the drain may be transparent. The front wall of the drain
may be translucent.

The drain may be provided with one or more pursing
strips. The or each pursing strip may span the width of the
drain. The or each pursing strip may extend the same
distance along the length of the drain. The or each pursing
strip may provide localised rigidity to the drain. The or each
pursing strip may be formed from polystyrene. The or each
pursing strip may define the locations and orientations of
one or more folds of the drain. The or each pursing strip may
comprise a strip of flexible material attached drain. The strip
may have a higher rigidity than the material of the drain. The
or each pursing strip may have some resilience once
attached to the drain. Therefore, the pursing strips can be
squeezed laterally to arch the pursing strip and thereby assist
in opening the drain.

A pursing strip may be provided on the rear wall. The
pursing strip may be provided adjacent a bottom end of the
drain. The pursing strip may be provided on the outside
surface of the rear wall. A pursing strip may be provided on
the front wall. The front wall pursing strip may be provided
on the outside surface of the front wall. The front wall
pursing strip may be provided above the rear wall pursing
strip. The front wall pursing strip may be provided midway
between a top end and the bottom end of the drain. A
longitudinal gap may be provided between an upper edge of
the rear wall pursing strip and a lower edge of the front wall
pursing strip. The longitudinal gap may define the location
of a first fold of the drain.

The or each pursing strip may have a colour with a value
in the range of L*=50.0 to 70.0, a*=+1.8 to +10.0 and
b*=−0.9 to −9.0 or +0.9 to +12.0 (or more preferably +1.0
to +12.0) measured in the CIE L*a*b* colour code system
(described herein). The or each pursing strip may have a
colour with a value in any one of the narrower ranges
identified above in respect of the comfort layer on the front wall. Moreover, the colour of the or each pursing strip may
be in the same narrower range as the comfort layer on the
front wall.

A fastening element may be disposed on an outside
surface of the rear wall. The rear fastening element may be
disposed above the front pursing strip. A longitudinal gap
may be provided between an upper edge of the front wall
pursing strip and a lower edge of the second fastening
element. The longitudinal gap may define the location of a
fold of the drain. The rear fastening element may be dis-
posed adjacent the top end of the drain.

A closure mechanism for the drain of the ostomy pouch
may be attached to a sheet of comfort material covering the
front of the pouch. The closure mechanism may be attached
to the outside surface of the comfort material. The closure
mechanism may be a closure flap. The closure flap may be
welded to the comfort material. It may be welded opposite
a region of hot melt adhesive. The weld may be along a top
edge of the closure flap. The closure flap may have an
outside surface and an inside surface. The inside surface of
the closure flap may be adjacent the outside surface of the
comfort material. The closure flap may comprise a front
fastening element. The front fastening element may co-
operate to fasten with the rear fastening element. Fastening
of the fastening elements may close the drain.

The closure flap may comprise a plastic foam material.
This is desirable as it imparts a rigidity desirable in a closure
flap in particular, to keep the folded drain flat.

The closure flap may comprise a comfort material (op-
tionally comprising the hot-melt adhesive, e.g. a web thereof
having the features set out above). This is desirable as
forming the closure flap of the same material as the comfort
material makes it more subtle/discreet.

The closure flap may extend across the majority of the
width of the pouch. It may conform to the shape of the
pouch. It may be arranged adjacent to a peripheral weld
between the front comfort layer and the front wall. Extend-
ing across substantially all of the width of the pouch is
unusual because normally closure flaps are attached not to
the comfort material but to the material of the drain and must
therefore be much narrower than the width of the pouch.

The closure flap may have a colour with a value in the
range of L*=50.0 to 70.0, a*=+1.8 to +10.0 and b*=−0.9 to
−9.0 or +0.9 to +12.0 (or more preferably +1.0 to +12.0)
measured in the CIE L*a*b* colour code system (described
herein). The closure flap may have a colour with a value in
any one of the narrower ranges identified above in respect of
the comfort layer on the front wall. Moreover, the colour of
the closure flap may be in the same narrower range as the
comfort layer on the front wall.

The front fastening element may be disposed above the
rear fastening element. The front fastening element may be
disposed adjacent a bottom edge of the comfort material. A
longitudinal gap may be provided between an upper edge of
the rear fastening element and a lower edge of the front
fastening element. The longitudinal gap may define the
location of a fold of the drain. The rear fastening element
may be disposed adjacent the top end of the drain.

The drain may be closed by repeatedly folding the drain
upwards about the fold lines defined by the front and rear
pursing strips and front and rear fastening elements. The
folded drain may be retained between the woven comfort
material and closure flap. The sides of the closure flap may
not extend beyond the edges of the comfort material. The
closure flap may comprise a tab. The tab may extend beyond
the bottom edge of the comfort material. The front and rear fastening elements may be the same size. The front and rear fastening elements may not span the width of the drain.

Therefore, the drain can be conveniently closed against the comfort material and secured in place with the closure flap. It is therefore not necessary to fold or secure the drain beneath the comfort material, making the pouch easier to use. The provision of a tab makes unfolding of the drain easier as the closure flap can be lifted allowing access to undo the fastening elements, as does the inclusion of fastening elements that do not span the entire drain width.

The closure flap may have a contoured outline, for example the outline of a segment of a circle, which can give the base of the pouch a rounded appearance. This is considered preferable as a flat bottom is typically associated with "open" pouches (caused by the folding up of a drain at the bottom) whereas a rounded bottom may be seen as more stylish and not associated with the somewhat unpleasant draining process. Thus, although the pouch may be an open pouch the closure flap may make that less obvious.

According to a second aspect of the present invention, there is provided a method of forming an ostomy pouch, the method comprising: providing a rear wall and a front wall which define a cavity for containing stomal output; providing an inlet in the rear wall for receiving human waste; and applying a sheet of comfort material to the front wall; wherein at least the comfort layer on the front wall has a colour with a value in the range of $L^*=50.0$ to $70.0$, $a^*=+1.8$ to $+10.0$ and $b^*=-0.9$ to $-9.0$ or $+0.9$ to $+12.0$ measured in the CIE $L^*a^*b^*$ colour code system (described herein). The colour preferably has a value in the range of $L^*=50.0$ to $70.0$, $a^*=+1.8$ to $+10.0$ and $b^*=-0.9$ to $-9.0$ or $+1.0$ to $+12.0$ The second aspect may comprise forming an ostomy pouch according to the first aspect of the invention, optionally including any optional feature thereof.

According to a third aspect of the present invention, there is provided a method for collecting stomal output using an ostomy pouch according to the first aspect of the invention, optionally including any optional features and optionally manufactured according to the second aspect of the invention. The method may comprise attaching the ostomy pouch about a stoma of an ostomate. The ostomy pouch may be attached about the stoma through use of an ostomy wafer of the pouch where the pouch comprises a one-piece ostomy pouch. Alternatively, the method may comprise attaching an ostomy wafer of a body fitment component of a two-piece ostomy pouch about the stoma; and attaching a pouch to the body fitment component. The pouch may be attached to the body fitment component before or after the ostomy wafer has been attached about the stoma. Where the ostomy pouch comprises an open or drainable pouch, the method may comprise draining stomal output from the ostomy pouch.

DETAILED DESCRIPTION OF THE INVENTION

In order that the invention may be more clearly understood one or more embodiments and examples thereof will now be described, by way of example only, with reference to the accompanying drawings, of which:

Unless defined otherwise, all technical and scientific terms used in this specification have the same meaning as is commonly understood by the reader skilled in the art to which the claimed subject matter belongs. It is to be understood that the foregoing summary of the disclosure and the following examples are exemplary and explanatory only and are not restrictive of any subject matter claimed. Notably, the invention is primarily concerned with colour, rather than the precise structure of an ostomy device.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

In this specification, the use of the singular includes the plural unless the context clearly dictates otherwise. In this application, the use of "or" means "and/or" unless stated otherwise. Furthermore, use of the term "including" as well as other forms, such as "include", "includes," and "included," is not limiting.

Figure 2:
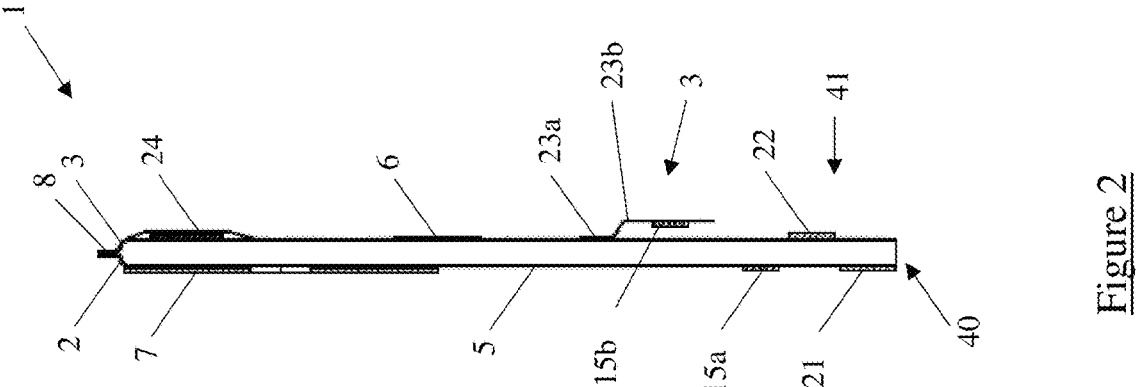
FIG. 2 is a cross-sectional side view of the ostomy pouch of FIG. 1.
Figure 1:
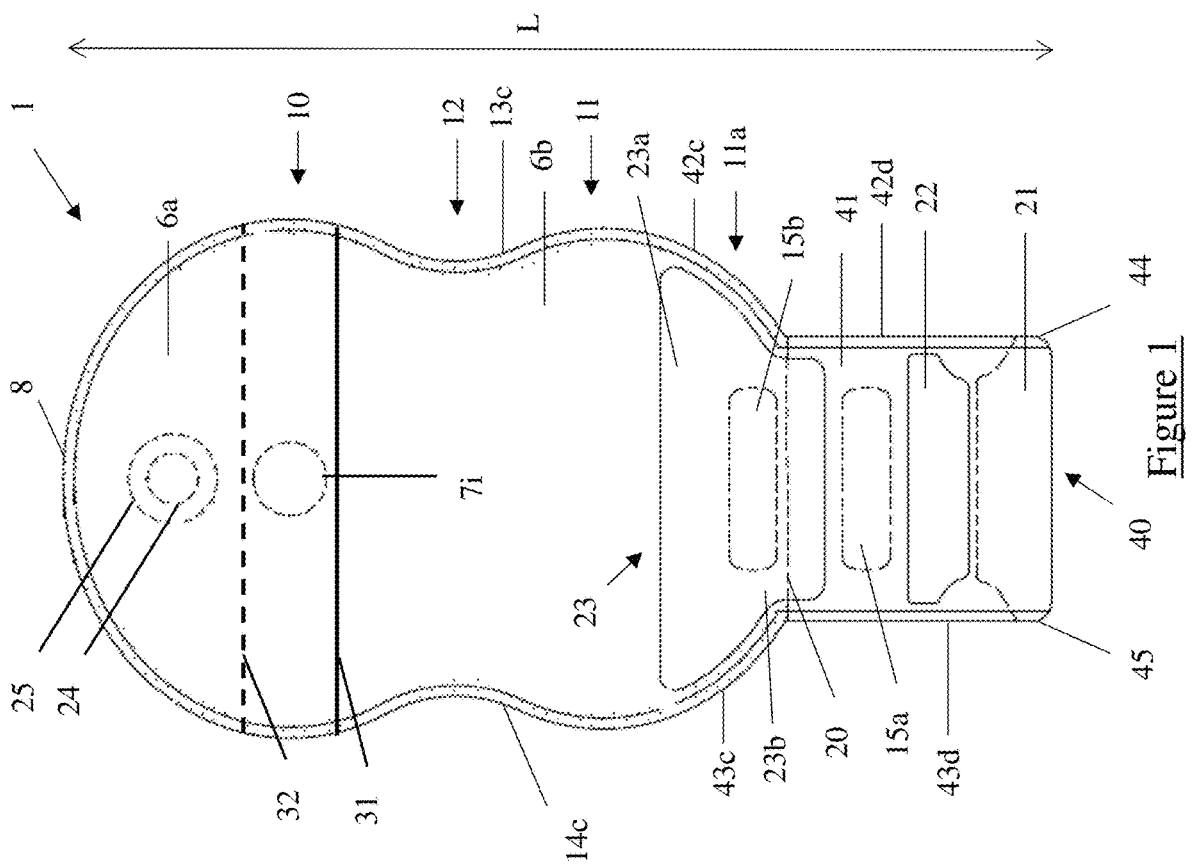
FIG. 1 is a front view of an alternative ostomy pouch.
Figure 3:
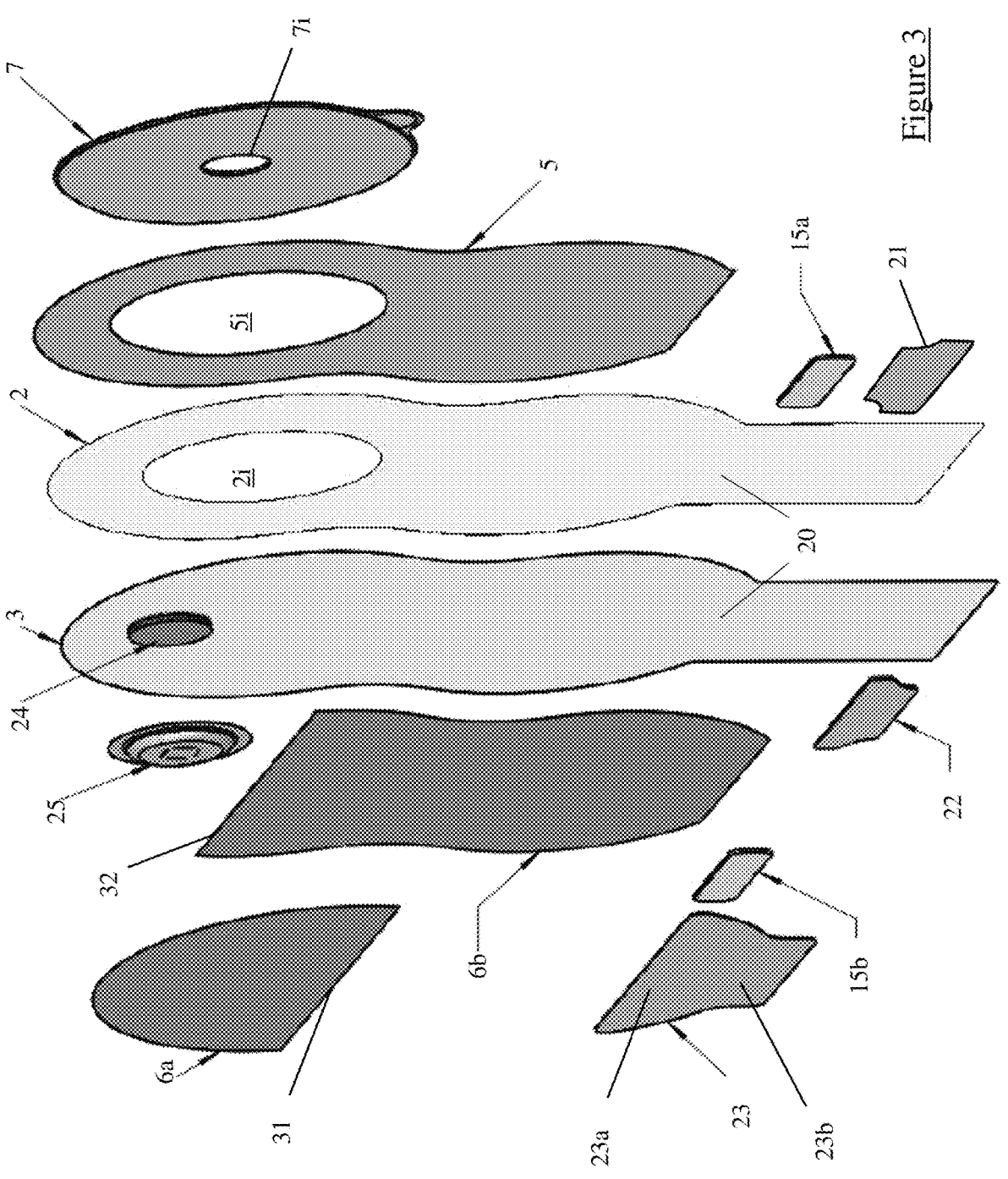
FIG. 3 is an exploded perspective view of the ostomy pouch of FIG. 1.

Referring to FIGS. 1 to 3, an embodiment of an "open" ostomy pouch 1 which has a foldable drain. Those skilled in the art will understand that the invention could apply equally to "closed" ostomy pouches.

The pouch comprises front 3 and rear 2 walls. The front wall 3 is formed of a transparent film, whilst the rear wall 2 is formed of an opaque film. The rear wall 2 features a large opening 2i in register with the stomal inlet 7i of a wafer 7 (which is connected to the rear wall 2 in the region between the periphery of the opening 2i and the periphery of the wafer, such that stomal output enters the cavity via the stomal inlet of the wafer and the opening 2i in the rear wall).

A rear comfort layer 5 is provided on the rear wall and also features an opening 5i slightly larger than the opening 2i in the rear wall 2 and in register with it, so as to be sandwiched between the outermost edge of the wafer and the rear wall 2. The stomal inlet 7i is adjustable to fit the stoma of the ostomate.

A front comfort layer 6 is provided on the front wall 3; the front comfort layer 6 of this embodiment is formed of two parts: an upper part 6a; and a lower part 6b. The upper part 6a overlaps the lower part 6b across the width of the pouch 1 at a point on its height in register with the stomal inlet 7i. The overlap being defined by the lower edge 31 of the upper part 6a that overlaps the upper edge 32 of the lower part 6b.

The overlap provides an opening, whereby the upper part 6a and lower part 6b can be pulled apart so that the ostomate/user can view the stoma or the contents of the pouch through the (transparent) front wall 3

In this embodiment, there is also an optional gas filter 24 positioned in the front wall 3 at a height above the stomal inlet 7i to allow gas to exit the pouch 1. in this embodiment, the filter 24 is covered by an optional filter cover patch 25 (not shown in FIG. 2) on the outside surface of the front wall 3. As such, the filter 24 and filter cover patch 25 are covered by the upper part 6a of the front comfort layer 6.

In this embodiment, the drain extends from the lower edge of the ostomy pouch 1; the lower section 11 of the pouch 1 comprises a drain aperture 40. The drain aperture 40 is an unsealed portion of the perimeter of the ostomy pouch 1 where the rear 2 and front 3 walls are not sealed.

In this embodiment, the lower section 11 comprises a rounded portion 11a and a substantially rectangular drain portion 41 that accommodates the drain aperture 40, with the rounded portion 11a being adjacent a waisted section 12 and the drain portion 41 being distal the waisted section 12. The drain portion 41 is foldable along its length between an unfolded and a folded configuration.

In this embodiment, the lower section 11 comprises a continuous left edge 42 that extends from the left edge 13c of the waisted section 12 to a left vertex 44 of the drain aperture 40 around the curved left edge 42c of the generally rounded portion 11a and along a left edge 42d of the drain portion 41. Similarly, a continuous right-hand edge 43 extends from the right edge 14c of the waisted section 12 to a right vertex 45 of the drain aperture 40 around a continuously curved right edge 43c of the generally rounded portion 11a and along a right edge 43d of the drain portion 41. (Note that as FIG. 1 is a front view, the left edges of the pouch 1 are on the right of the figure and right edges of the pouch 1 on the left of the figure.)

In this embodiment, a single continuous edge seal 8 extends around the perimeter of the pouch 1 from the left vertex 44 of the drain aperture 40 to the right vertex 45 of the drain aperture 40, leaving the distal end of the drain aperture 40 open.

In this embodiment, the drain portion 41 defines an elongate drain passage that extends from the cavity of the ostomy pouch 1 to the drain aperture 40 located at a lower end of the drain portion 41. The drain portion 41 is integral with the lower section 11 and as such, the rear wall 2 and the front wall 3 may each be a single piece of material that includes the upper section 10, the waisted section 12 and lower section 11 (including the drain portion 41). However, in this embodiment, the rear comfort layer 5 and front comfort layer 6 do not cover the drain portion 41 of the rear wall 2 and the front wall 3.

In this embodiment, communication between the cavity and the elongate drain passage is via a drain inlet 20 defined as the point of transition between the cavity and the drain portion 41. The drain inlet 20 allows passage of stomal output from the cavity into the drain portion 41 when the drain portion 41 is unfolded.

Movement of the drain portion 41 between its unfolded or folded configuration opens or closes the drain aperture 40. This either permits or prevents outflow of the stomal output stored in the ostomy pouch cavity.

In this embodiment, the drain portion 41 can be repeatedly folded in the same sense along its length into a plurality of segments having approximately equal segment lengths and separated by folds. The drain portion 41 may therefore be successively folded one or more times such that the segments overlie each other. Each fold is formed across the width of the drain portion 41 and acts to inhibit and preferably prevent passage of stomal output out of the drain aperture 40.

In this embodiment, first 21 and second 22 pursing strips are provided on the drain portion 41. The pursing strips 21, 22 provide both localised rigidity to the drain portion 41 and also define the locations and orientations of the segments and folds of the drain portion 41. The pursing strips 21, 22 comprise strips of flexible material attached drain portion 41, wherein the strips 21, 22 have a higher rigidity than the material of the drain portion 41. The pursing strips 21, 22 also have some resilience such that once attached to the drain portion 41, the pursing strips 21, 22 can each be squeezed laterally to arch the pursing strip and thereby open the elongate drain passage. In other embodiments, two or more pursing strips may be used.

In this embodiment, the pursing strips 21, 22 are formed from polystyrene, but other embodiments may comprise any suitable material.

In this embodiment, the first pursing strip 21 is attached to the rear wall 2 of the drain portion 41 adjacent the drain aperture 40. The second pursing strip 22 is attached to the front wall 3 of the drain portion 41 above the second strip 22. A longitudinal gap is provided between an upper edge of the first pursing strip 21 and a lower edge of the second pursing strip 22. The longitudinal gap therefore defines the location of a first fold of the drain portion 41. Each pursing strip 21, 22 spans the width of the drain portion 41 and extends the same distance along a length of the drain portion 41.

In this embodiment, a rear fastening element 15a is arranged on the rear wall 2 and a front fastening element 15b is arranged on a flap 23 that is mounted to the front comfort layer 6. In this example of a two-part front comfort layer 6, the flap 23 is mounted to the lower part 6b of the comfort layer 6. The rear fastening element 15a and the front fastening element 15b comprise corresponding hook-and-loop type fastener elements. The rear fastening element 15a is located on the drain portion 41 above the second pursing strip 22. A longitudinal gap is provided between an upper edge of the second pursing strip 22 and a lower edge of the rear fastening element 15a. The longitudinal gap therefore defines the location of a second fold of the drain portion 41.

In this embodiment, the flap 23 comprises a first flange 23a and a second flange 23b formed of one integral piece. The first flange 23a spans substantially all of the width of the lower rounded section 11a, but does not extend over the edge seal 8, at a point one third up the length of the rounded section 11a from the drain inlet 20. The first flange 23a is attached to the comfort material 6 by a line of adhesive that spans substantially its entire width. The second flange 23b extends from the lower edge of the first flange 23a and is connected to the pouch 1 only by the first flange 23a. The second flange 23b is contoured so as to conform to the shape of the rounded portion 11a but is thinner, tracing the inside edge of the peripheral weld 8. As such, the second flange 23b extends downwards from the first flange 23a within the perimeter defined by the edge seal 8 of the pouch 1.

In this embodiment, the flap 23 has an outside surface, facing away from the ostomate in use and an opposite inside surface. The front fastening element 15b is located on the inside surface of the second flange 23b at a position above the rear fastening element 15a. A longitudinal gap is provided between an upper edge of the rear fastening element 15a and a lower edge of the front fastening element 15b and defines the location of a third fold of the drain portion 41. The flap 23 is formed from a flexible sheet material that is more rigid than the flexible sheet material of the rear wall 2, front wall 3 and comfort layers 5, 6. In this embodiment, the flap 23 is formed from a plastic foam which provides a desirable rigidity.

Folding of the drain portion 41 may be carried out as follows. First, the distal end of the drain portion 41 is folded upwards and away from the rear of the ostomy pouch 1 about the first fold line to locate the first pursing strip 21 over the second pursing strip 22. Secondly, the drain portion 41 and the pursing strips 21, 22 are folded again, in the same sense, about the second fold line and then the third fold line such that the folded and stacked first pursing strip 21, second pursing strip 22 and first fastening element 15a are located beneath the second flange 23b of the flap 23 with the rear fastening element 15a being exposed and adjacent the front fastening element 215b. Finally, the second flange 23b of the flap 23 is pressed onto the folded drain portion to secure together the rear fastening element 15a and the front fastening element 15b.

In these embodiments, the drain portion 41 can then be unfolded by reversing the above procedure.

The rear comfort layer 5 and the front comfort layer 6 are formed of a flexible sheet material comprised of a woven fabric layer with a web of hot-melt adhesive coated on one surface—its inside surface in use. In this embodiment, the fabric layer forms the outside surface of the rear 5 and front 6 comfort layers respectively, with the web of hot-melt adhesive disposed on the corresponding inside surfaces, facing the rear 2 and front 3 walls. Other embodiments may comprise additional fabric layers and/or adhesive layers as required. In this embodiment, the woven fabric layer comprises polyester but in other embodiments any one or more of nylon, viscose, polyethylene and polypropylene could be used in addition or as an alternative.

In this embodiment, the woven fabric layer has an area density of 58 g/m$^2$, a tensile strength of 620 N, and a tear strength of 16 N. Other embodiments may have different compositions, for example an area density of 40 to 80 g/m$^2$, a tensile strength of 200 to 800 N, and a tear strength of 10 to 30 N. Some embodiments may also have a colour fastness to any one or more of rubbing, perspiration or washing (40°) of 4 to 5, and an abrasion of >50,000 rub cycles.

A suitable woven polyester layer is available from Newton Textiles Limited of Northamptonshire, UK, under the 75DCWR Designation, such as 75DCWRTAUPE (for a mauve coloured variant). Other suitable woven layers include a woven polyester layer manufactured by PANTONE LLC of CARLSTADT NJ, UNITED STATES under the designation TCX 15-3800 and woven cotton layers also manufactured by PANTONE LLC of CARLSTADT NJ, UNITED STATES under the designations TCX 18-3710; TCX 18-4017; TCX18-1108; and TCX 18-1321 (of which TCX 18-4017 and TCX 18-1321 are also available from mode . . . information Ltd. of London, ENGLAND).

In this embodiment, the hot-melt adhesive comprises ethylene-vinyl acetate (EVA) A suitable EVA hot-melt adhesive is available from Protechnic SA of Cernay, France, under the designation CZ8D25 and described by Protechnic SA as a web.

The hot-melt adhesive is coated onto the fabric layer over an entire area of the rear 5 and the front 6 comfort layers to form a web including a mass M of hot-melt adhesive with numerous voids V therein, where there is an absence (or substantial absence, possibly including a trace) of hot-melt adhesive, thus it takes the general form of a lattice, mesh or grid.

In this embodiment, a peripheral weld defined by an edge seal 8 also joins the rear comfort layer 5 to the rear wall 2 and the front comfort layer 6 to the front wall 3.

In this exemplary preferred embodiment, the front wall 3 is transparent to allow viewing of the contents of the pouch, whereas both parts of the front comfort layer 6, the rear comfort layer 5, the rear wall 2 (part of which forms the drain) and the pursing strips all have a colour with a value in the range of L*=50.0 to 70.0, a*=+1.8 to +10.0 and b*=−0.9 to −9.0 or +0.9 to +12.0 (preferably +1.0 to +12.0) measured in the CIE L*a*b* colour code system (described herein).

Examples

Examples of comfort materials for forming the comfort layer on the front wall of an ostomy pouch comprising a front wall, a rear wall and an inlet for receiving human waste have been obtained and compared with comparative examples. The comfort materials of the examples have a colour with a value in the range of L*=50.0 to 70.0, a*=+1.8 to +10.0 and b*=−0.9 to −9.0 or +0.9 to +12.0 (preferably +1.0 to +12.0) measured in the CIE L*a*b* colour code system (described herein).

Example 1 is a woven polyester layer available from PANTONE LLC of CARLSTADT NJ, UNITED STATES under the designation TCX 15-3800; Example 2 is a woven cotton layer manufactured by PANTONE LLC of CARLSTADT NJ, UNITED STATES under the designation TCX 18-3710; Example 3 is also woven cotton from PANTONE LLC sold under the designation TCX 18-4017; Example 4 is also woven cotton from PANTONE LLC sold under the designation TCX 18-1108; and Example 5 is also woven cotton from PANTONE LLC sold under the designation TCX 18-1321.

Comparative Examples 1, 3, 4 and 5 are also woven cotton layers from PANTONE LLC with designations TCX 12-2905; TCX 13-4015; and TCX 13-3406 respectively. Comparative Example 2 is woven polyester taken from a pouch sold by COLOPLAST LTD of Peterborough, ENGLAND.

Tests have been undertaken to compare two aspects of pouches having comfort materials in the goldilocks range outlined above: 1, visibility of the pouch material through clothes when dry, referred to as a "visibility test"; and 2: visibility through the comfort material of the pouch when wet, referred to as a "transparency test".

Visibility Test

The visibility test approximates, but seeks to improve upon, the visibility test conducted in EP2755613 to compare the examples therein. Accordingly, the visibility of a swatch of material for an ostomy bag was tested by a test panel of 10 persons performing a subjective visual test under conditions as close as possible to daily life conditions.

In order to match a broad variety of skin tones, we obtained mannequins in Caucasian and African skin colours for use for the test. Colour samples were mounted on the mannequins in positions corresponding to that of an ostomy bag and covered with a shirt made of white textile. White textile was chosen as white being the most sensitive colour in a visibility test as it is bright and neutral as well as often appearing relatively transparent/translucent; use of a mannequin and an actual shirt was used to best replicate real life.

The colour samples were all made of the either woven polyester or woven cotton with both examples and comparative examples in cotton and examples and comparative examples in polyester. The different material was not found to influence the result.

The test samples were viewed in daylight by the test panel, rating the samples with a character of 1-8, "8" being the most visible to "1" being the most invisible. The colour of the test samples were determined by the CIE L*a*b* colour code system and are compared and against both a comparative example (Comparative Example 1) in pink skin colour close to that currently sold by ConvaTec Limited and a comparative example (Comparative Example 2) as sold by Coloplast® which is understood to fall within the grey range defined in EP2755613, alongside two comparative examples (Comparative Examples 3 and 4) with similar a* and b* values to the examples of the invention, but L* values outside the range and a fifth comparative example (Comparative Example 5) with a* and b* values around those of claimed in EP2755613, but again an l* value outside the range. The results from the test are shown in Table 1 below.

The test shows that the colours in the goldilocks range are at least comparable in invisibility to that of the pink skin and the coloplast comparative example which is understood to fall within the range of EP2755613.

TABLE 1

| | Sample | | CIE L*a*b | | | Visibility | |
| | | | | | | African | Caucasian |
| No. | Colour | L* | a* | b* | | skin | skin |
|---|---|---|---|---|---|---|---|
| Comparative example 1 | Pink skin Pantone TCX: 12-2905 | 86.2 | 12.3 | −2.7 | | 2.36 | 2.18 |
| Comparative example 2 | Greyish (Coloplast commercial product) | ? | ? | ? | | 1.09 | 2.45 |
| Comparative example 3 | "Lilac Hint" Pantone TCX: 13-4015 | 83.7 | 1.9 | −4.9 | | 1.27 | 3.30 |
| Comparative example 4 | "Orchid Ice" Pantone TCX: 13-3406 | 85.0 | 7.5 | −3.4 | | 1.45 | 2.0 |
| Comparative example 5 | "Nimbus Cloud" Pantone TCX: 13-4108 | 85.3 | 0.5 | 1.5 | | 1.64 | 4.45 |
| Example 1 | "Porpoise" Pantone TCX: 15-3800 | 68.0 | +2.5 | +2.1 | | 1.18 | 3.18 |
| Example 2 | "Grey Ridge" Pantone TCX: 18-3710 | 52.2 | 6.7 | −5.5 | | 1.36 | 5.5 |
| Example 3 | "Night Owl" Pantone TCX: 18-4017 | 50 | 1.8 | −4.8 | | 1.64 | 4.0 |
| Example 4 | "Fallen Rock" Pantone TCX: 18-1108 | 50.3 | 1.9 | 8.7 | | 1.45 | 3.82 |
| Example 5 | "Brownie" Pantone TCX: 18-1321 | 50.5 | 9.4 | 11.5 | | 1.00 | 2.91 |

It may be noted that example 2 in particular was found to be relatively visible against Caucasian skin (with the only value above ⅘ (i.e. more visible than invisible). As such, example 2 could in practice be less suitable for use by Caucasians who wear white shirts, but would still be of value to those with darker skin-tones, and of course to Caucasian people, to whom transparency when wet is a more important factor (and/or who tend to wear darker clothes) as will be seen by the results of the transparency test below.

Transparency Test

The transparency test looks at how see-through the examples become when wet (to simulate the effect of wearing the pouch in the shower)—in particular this test establishes how visible a typical coloured solid stomal output is when that output is viewed through a saturated piece of sample comfort material.

Accordingly, the visibility of stomal output in an ostomy bag was tested by a test panel of 10 persons performing a subjective visual test under conditions as close as possible to daily life conditions.

Test-sample ostomy pouches with two transparent film walls 2, 3 were prepared, then a swatch of fabric of each sample colour was applied to each side as a comfort layer 5, 6 and an equal amount of "foo" (a fake output simulating a typical output in terms of colour and consistency), was introduced into each test sample ostomy pouch and each pouch was mounted on a test wall (via a wafer 7).

The test samples were viewed in daylight by the test panel, rating the samples with a character of 1-8, "8" being the most visible stomal output (i.e. the most transparent cover layer) to "1" being the most invisible (i.e. the most opaque cover layer). Obviously, again, this test a lower score is preferable as it indicates a less transparent material, more suited for use when publicly bathing etc.

The test samples and comparative examples were the same as in the first test. And the results from the test and the standard are shown in Table 2 below.

The test shows that the colours in the goldilocks range are all slightly less transparent when dry as that of EP2755613 and the pink skin colour, with all, including the comparative example being less than 4.0, i.e. more opaque than transparent, and all deemed more than acceptably opaque. The more important figures concern transparency when wet, where it can be seen that the examples within the Goldilocks range are substantially less transparent when wet (at least to a typical stomal output in a pouch). Each of the comparative examples scores 6.0 or more out of 8 and is considered unacceptably transparent, whereas the examples of the invention score between less than 5, with some even less than 3 indicating at least adequate opacity and and in many cases very opacity, even in an environment similar to that which would be encountered in a swimming pool or shower.

TABLE 2

| | Sample | | CIE L*a*b | | | Transparency | |
| No. | Colour | L* | a* | b* | | Dry | Wet |
|---|---|---|---|---|---|---|---|
| Comparative example 1 | Pink skin Pantone TCX: 12-2905 | 86.2 | 12.3 | −2.7 | | 2.73 | 6.91 |
| Comparative example 2 | Greyish (Coloplast commercial product) | ? | ? | ? | | 3.09 | 6.36 |
| Comparative example 3 | "Lilac Hint" Pantone TCX: 13-4015 | 83.7 | 1.9 | −4.9 | | 2.27 | 6.82 |
| Comparative example 4 | "Orchid Ice" Pantone TCX: 13-3406 | 85.0 | 7.5 | −3.4 | | 3.18 | 6.00 |
| Comparative example 5 | "Nimbus Cloud" Pantone TCX: 13-4108 | 85.3 | 0.5 | 1.5 | | 2.3 | 6.18 |
| Example 1 | "Porpoise" Pantone TCX: 15-3800 | 68.0 | +2.5 | +2.1 | | 1.73 | 4.45 |
| Example 2 | "Grey Ridge" Pantone TCX: 18-3710 | 52.2 | 6.7 | −5.5 | | 1.09 | 3.09 |
| Example 3 | "Night Owl" Pantone TCX: 18-4017 | 50 | 1.8 | −4.8 | | 1.36 | 3.00 |
| Example 4 | "Fallen Rock" Pantone TCX: 18-1108 | 50.3 | 1.9 | 8.7 | | 1.09 | 1.82 |
| Example 5 | "Brownie" Pantone TCX: 18-1321 | 50.5 | 9.4 | 11.5 | | 1.09 | 2.73 |

Determination of Colour

A colour may be defined in many ways. Two of the most recognized colour systems are the CMYK colour model and the CIE L*a*b* system. The colour of the ostomy bag of the present invention has been determined only with the CIE L*a*b* because the CMYK model involves visual comparison with colour standards that are defined by the CMYK colour model, whereas the CIE L*a*b* can be conducted reproducibly using a spectrophotometer. The colour can be determined using a spectrophotometer of the type Sphere d/8°, details as follows:

Spectrophotometer for colour measurements, type SP64 Series, Manufacturer: X-Rite. The settings were the following: Target window: 4 mm (size of measuring area), Light sourceD65/10°, Specular component SPIN (Specular component included—SCI. Non UV filter) and room temperature 22.5° C. Measured over black background. The colours were represented by (CIE) Colour Standards Committee Systems.

L*: Lightness/Darkness (Value: 0-100) White is 100 and black is 0.

a*: Red/Green coordinate Positive value=Red, negative value=Green b*: Yellow/Blue coordinate Positive value=Yellow, negative value=Blue h°: Hue (Value: 0-360°) The hue angle indicates the colour.

C*: Chroma (Value: 0-100) Gray is 0 and 100 is a fully saturated colour.

Standard tolerance: CMC2: i: L*=2, h°=Variable ellipse, C=1, Cf=1 (Commercial factor expends ellipse).

The one or more embodiments and examples are described above by way of example only. Many variations are possible without departing from the scope of protection afforded by the appended claims.

The invention claimed is:

1. An ostomy pouch, comprising:
a front wall;
a rear wall;
an inlet for receiving human waste; and
the pouch having a comfort layer provided at least on the front wall;
wherein at least the comfort layer on the front wall has a colour with a value in the range of L*=50.0 to 70.0, a*=+1.8 to +10.0 and b*=−0.9 to −9.0 or +0.9 to +12.0 measured in the CIE L*a*b* colour code system.

2. The ostomy pouch according to claim 1 wherein L* is 65.0-70.0 a* is +2.4 to +2.6 and b* is +2.0 to +2.2.

3. The ostomy pouch according to claim 1 wherein L* is 50.0-55.0 b* is −4.5 to −5.5 and a* is +6.5 to +7.0.

4. The ostomy pouch according to claim 1 wherein L* is 50.0-55.0 b* is −4.5 to −5.5 and a* is +1.8 to +2.0.

5. The ostomy pouch according to claim 1 wherein L* is 50.0-55.0 a* is +1.8 to 2.0 and b* is +8.5 to +8.9.

6. The ostomy pouch according to claim 1 wherein L* is 50.0-55.0 a* is +9.3 to +9.5 and b* is +11.3 to +11.7.

7. The ostomy pouch according to claim 1 further comprising a comfort layer on the rear wall.

8. The ostomy pouch according to claim 7 wherein the comfort layer on the rear wall has the same colour as the comfort layer on the front wall.

9. The ostomy pouch according to claim 7 wherein the comfort layer on the rear wall has a contrasting colour to that on the front wall, having a lower L* value in the CIE L*a*b* colour code system.

10. The ostomy pouch according to claim 1, wherein the front wall on which at least one comfort layer is formed is transparent or translucent and wherein there are no opaque intervening walls between the front wall and the comfort layer provided thereon.

11. The ostomy pouch according to claim 1, wherein the at least one comfort layer formed on the front wall is spaced from the front wall.

12. The ostomy pouch according to claim 1, wherein an opening is provided in the comfort layer provided in the front wall, through which an ostomate may inspect stomal output.

13. The ostomy pouch according to claim 1, wherein the comfort layer comprises a sheet of absorbent woven comfort material.

14. The ostomy pouch according to claim 1, wherein the comfort layer comprises a sheet of comfort material having an outside surface and an opposite inside surface, the outside surface of the sheet of comfort material forming at least part of the outside surface of the pouch, and at least part of the sheet of comfort material having a hot-melt adhesive applied as a web to the inside surface of the sheet of comfort material, the web comprising a mass and a plurality of voids in the mass.

15. The ostomy pouch according to claim 1, comprising:
a cavity for storing stomal output, the cavity defined by the rear wall and the front wall;
wherein the rear wall and front wall are formed of flexible plastic film, joined at their peripheries;
wherein the rear wall is opaque and the front wall is transparent or translucent;
wherein the rear wall and front wall each have corresponding inside and outside surfaces whereby the inside surfaces of the rear and front walls form the interior of the cavity and the outside surfaces of the rear and front walls form the exterior of the cavity;
wherein the comfort layer is covering the outside surface of the front wall, but able to be spaced from and separable from the front wall.

16. The ostomy pouch according to claim 1, comprising a drain; the drain having a front wall and a rear wall; and the rear wall of the drain having a colour with a value in the range of L*=50.0 to 70.0, a*=+1.8 to +10.0 and b*=−0.9 to −9.0 or +0.9 to +12.0 measured in the CIE L*a*b* colour code system; and the front wall of the drain being transparent or translucent.

17. The ostomy pouch according to claim 1 wherein L* is 50-59.9 a* is +1.8 to +10.0 and b* is +1.00.9 to +12.0.

18. The ostomy pouch according to claim 1 wherein the CIE L*a*b* values defined are determined with a spectrophotometer of the type Sphere d/8°, SP64 Series, Manufacturer: X-Rite with the following settings: Target window: 4 mm, size of measuring area; Light source D65/10°; Specular component SPIN, Specular component included—SCI, Non UV filter; and room temperature 22.5° C.; measured over black background; the colours were represented by (CIE) Colour Standards Committee Systems:

L*: Lightness/Darkness (Value: 0-100) White is 100 and black is 0 a*: Red/Green coordinate Positive value=Red, negative value=Green b*: Yellow/Blue coordinate Positive value=Yellow, negative value=Blue h°: Hue (Value: 0-360°) The hue angle indicates the colour C*: Chroma (Value: 0-100) Gray is 0 and 100 is a fully saturated colour Standard tolerance: CMC2: i: L*=2, h°=Variable ellipse, C=1, Cf=1 (Commercial factor expends ellipse).

19. A method of forming an ostomy pouch, the method comprising:
providing a rear wall and a front wall which define a cavity for containing stomal output;
providing an inlet in the rear wall for receiving human waste; and
applying a sheet of comfort material to the front wall;
wherein at least the comfort layer on the front wall has a colour with a value in the range of L*=50.0 to 70.0, a*=+1.8 to +10.0 and b*=−0.9 to −9.0 or +0.9 to +12.0 measured in the CIE L*a*b* colour code system.

20. The ostomy pouch according to claim 13 wherein the absorbent woven comfort material is one or more of polyester and cotton.

\* \* \* \* \*